US007101831B2

(12) United States Patent
Hoelderich et al.

(10) Patent No.: US 7,101,831 B2
(45) Date of Patent: Sep. 5, 2006

(54) COMPOSITIONS OF MATERIAL, ESPECIALLY LUBRICANTS AND PRESSURE TRANSMITTING MEANS, THE PRODUCTION AND USE THEREOF

(75) Inventors: Wolfgang Hoelderich, Frankenthal (DE); Ulrich Keller, Aachen (DE); Jutta Fischer, Leverkusen (DE); Patrick Weckes, Willich (DE); Theo Mang, Weinheim (DE); Rolf Luther, Speyer (DE); Helena Wagner, Mannheim (DE)

(73) Assignee: Fuchs Petrolub AG, Mannheim (DE)

( * ) Notice: Subject to any disclaimer, the term of this patent is extended or adjusted under 35 U.S.C. 154(b) by 437 days.

(21) Appl. No.: 10/181,710

(22) PCT Filed: Jan. 19, 2001

(86) PCT No.: PCT/EP01/00594

§ 371 (c)(1),
(2), (4) Date: Sep. 12, 2002

(87) PCT Pub. No.: WO01/53438

PCT Pub. Date: Jul. 26, 2001

(65) Prior Publication Data

US 2003/0186823 A1 Oct. 2, 2003

(30) Foreign Application Priority Data

Jan. 21, 2000 (DE) ................. 100 02 515
Jan. 21, 2000 (DE) ................. 100 02 516
Mar. 24, 2000 (DE) ................. 100 14 922

(51) Int. Cl.
*C10M 101/00* (2006.01)
*C07C 59/00* (2006.01)

(52) U.S. Cl. ............. 508/452; 554/121; 554/161
(58) Field of Classification Search ........... 554/121, 554/161; 508/452
See application file for complete search history.

(56) References Cited

U.S. PATENT DOCUMENTS 2,115,341 A    4/1938  Mikeska et al.
3,676,500 A    7/1972  Mantell et al.
4,083,816 A *  4/1978  Frankel et al. ............. 524/313
4,709,097 A    11/1987 Hoelderich et al.
5,698,722 A *  12/1997 Cusumano et al. ......... 554/219
6,420,322 B1 * 7/2002  Kodali ....................... 508/452

OTHER PUBLICATIONS

Knight, H.B. et al., "Addition of Formic Acid to Olefinic Compounds. I. Monoölefinic Compounds", *Eastern Regional Research Laboratory*, Dec. 20, 1953, vol. 75, pp. 6212-6215.
Knight, H.B. et al., "New Method for Hydroxylating Long-Chain Unsaturated Fatty Acids, Esters, Alcohols, and Hydrocarbons", *The Journal of The American Oil Chemists' Society*, Jan. 1954, vol. 31, No. 1, pp. 1-5.
Munns, W.O. et al., "The Preparation of Hydroxystearic Acids from Red Oil (Commercial Oleic Acid)", *The Journal of The American oil Chemists' Society*, Jan. 1963, vol. 40, pp. 22-24.
Black, L.T. et al., "Acetoxylation of Methyl Oleate with A Resin Catalyst", *The Journal of The American Oil Chemists' Society*, May 1967, vol. 44, pp. 310-312.
McCusker, "Structural Aspects of Molecular Sieves", pp. 393-423.
Kessler, "Synthesis of Molecular Sieves", pp. 425-464.
Flanigen et al., "Aluminophosphate Molecular Sieves and the Periodic Table", *Synthesis*, pp. 103-112.
Black et al., "Acetoxylation of Methyl Oleate with a Resin Catalyst", J. Amer. Oil Chem. Soc., vol. 44, No. 5, 1967, pp. 310-312.
Tulloch, "Carbon-13 NMR Spectra of All the Isomeric Methyl Hydroxy- and Acetoxyoctadecanoates", Org. Magn. Reson., vol. 11, No. 3, 1978, pp. 109-115.
Database WPI, Section Ch, Week 199747, Derwent Publications Ltd., AN 1997-508813 & JP 09-241210 A (New Japan Chemical Co. Ltd.), Sep. 16, 1997.

* cited by examiner

*Primary Examiner*—Ellen M. McAvoy
(74) *Attorney, Agent, or Firm*—Foley & Lardner LLP

(57) ABSTRACT

The invention relates to novel compositions of matter which may advantageously be used as lubricants or pressure transfer media or else for functional liquids and lubricant additives. The lubricants according to the invention are the reaction products of an electro-philic addition of linear or branched, aliphatic or aromatic carboxylic acids, carboxylic anhydrides, carbonyl halides or novel neoacids to the double bonds of fatty acids, esters thereof and/or of other fatty acid derivatives and also of synthetic esters. Owing to their increased oxidation resistance compared to the starting materials and also their low toxicity, the novel class of synthetic esters based on oleochemicals may find use in novel environmentally compatible lubricants, pressure transfer systems, functional liquids and lubricant additives.

13 Claims, No Drawings

COMPOSITIONS OF MATERIAL, ESPECIALLY LUBRICANTS AND PRESSURE TRANSMITTING MEANS, THE PRODUCTION AND USE THEREOF

The present invention relates to compositions of matter which are suitable as lubricants and pressure transfer media comprising esters of fatty acids, of fatty acid derivatives and of mixtures thereof, and also to a process for preparing these esters according to the invention by adding carboxylic acids and/or carboxylic anhydrides and/or carbonyl halides to the double bond and/or double bonds of fatty acids, fatty acid derivatives or mixtures thereof, and also to the use of these esters according to the invention as environmentally compatible, easily biodegradable lubricants, lubricant components, lubricant additives, hydraulic oils, pressure transfer media, transmission oils and functional liquids.

PRIOR ART

In Germany alone, 520,000 t of lubricant per year pass into the environment via leakage in seals or pipes, during repairs, in oil accidents or by vaporization and atomization. The use of renewable raw materials, directly or in the form of their conversion products, not only saves fossil raw materials, but also equalizes the $CO_2$ balance and also avoids set-aside to reduce farming overproduction.

The limits of application for natural oils and the fatty acids derived from them result from their low stability toward thermal and oxidative loading and hydrolysis and also from the limited cold flow behavior, i.e. properties which can only gradually be influenced by adding chemical additives such as sulfonates, phenol derivatives or amines. Breeding measures to enrich certain fatty acids in the triglycerides of plant oils may lead to improvement in the technical properties. However, chemical conversions which can attack both the alcohol components and the acid components are more important.

The attack point for the oxidative aging of natural oils and the fatty acids derived from them are the double bonds contained therein, and the double bonds having (Z) conformation are especially easily attacked by oxygen to form peroxidic intermediates.

The oxidation stability of natural oils or of the fatty acids derived from them may be increased, for example, by partial hydrogenation of the polyunsaturated acids.

The addition of formic or acetic acid to methyl oleate and subsequent hydrolysis of the ester obtained is known [H. B. Knight, R. E. Koos, D. Swern, *J. Am. Chem. Soc.*, 1953, 75, 6212; H. B. Knight, R. E. Koos, D. Swern, *J. Am. Oil Chem. Soc.*, 1954, 31, 1]. Boiling anhydrous formic acid adds to oleic acid without catalysis to 80% conversion in 24 hours. If small quantities of perchloric acid are added, the reaction time is shortened to 5 minutes. Acetic acid adds to oleic acid without catalysis only to a negligible extent; catalysis by perchloric acid leads to 40% conversion in 15 minutes, and a threefold excess of acetic acid gives conversions of from 60 to 70% after 70 hours [W. O. Munns, S. Kairys, D. A. Manion, *J. Am. Oil Chem. Soc.*, 1963, 40, 22].

The aim of all the processes described is not the preparation of the formyloxy or acetoxy compounds, but instead the hydrolysis thereof to give monohydroxystearic acid, which is an important component in preparing lubricant fats and oils and also plasticizers.

The acetoxylation to obtain the monoesters which are of industrial interest as plasticizers of PVC has been investigated under catalysis with the acid ion exchanger Amberlyst 15 [L. T. Black, R. E. Beal, *J. Am. Oil Chem. Soc.*, 1967, 44, 310]. At a methyl oleate/catalyst mass ratio of two and a 50-fold molar excess of acetic acid, 42% yields of methyl acetoxystearate were obtained over a period of 8 hours. When formic acid was used, no catalytic effect of Amberlyst 15 could be detected. The addition of propionic and butyric acid was likewise investigated, but these acids gave lower yields than acetic acid. No branched carboxylic acids were used. However, no systematic investigation of the rheological properties of the adducts obtained was carried out. The regeneration of the catalyst is not described in the literature. The aim of these experiments was an alternative route of preparing methyl monohydroxystearates, which are obtained by hydrolysis of the methyl acetoxy- and formyloxystearate intermediates.

None of the acyloxylations of fatty acids or fatty acid derivatives known from the literature mentions or makes known the use of reaction products as lubricants and/or pressure transfer media.

The described processes based on fatty acids, natural fatty acid derivatives and mixtures thereof provide novel materials for lubricants which surprisingly improve the critical properties of these natural crude products such as low aging stability, low oxidation stability, low hydrolysis stability and critical cold properties, without adversely affecting their advantages such as good lubricity or low viscosity dependence on temperature. The flexibility of the reaction allows certain properties such as viscosity, cold properties and elastomer compatibility to be set to specific values within wide ranges.

According to the invention, novel lubricants and pressure transfer media based on fatty acids and/or fatty acid derivatives have been found which are acyloxylated at at least one double bond, preferably by unbranched or branched carboxylic esters, in particular those of the general chemical formula I:

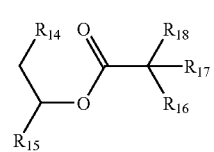

Formula I where $R_{14}$ is a carboxylic acid radical R—COOH where R is an alkyl, alkenyl, dienyl or polyenyl radical having from 2 to 20 carbon atoms and from 0 to 4 double bonds, preferably having from 3 to 11 carbon atoms and from 0 to 2 double bonds, for example, n-carboxyheptyl, n-carboxyundecyl, n-carboxy-4-heptenyl or esters thereof with monoalcohols, diols or polyols, such as methanol, ethanol, glycerol, pentaerythritol or trimethylolpropane;

where $R_{15}$ is an alkyl, alkenyl, dienyl or polyenyl radical having from 2 to 20 carbon atoms and from 0 to 4 double bonds, preferably from 3 to 14 carbon atoms and from 0 to 3 double bonds, in particular from 3 to 10 carbon atoms and from 0 to 2 double bonds, for example, n-hexyl, n-octyl, 2-octenyl or 2,5-octadienyl; and where $R_{16}$ is H or $R_{16}$ is an alkyl radical having from 1 to 10 carbon atoms, for example
methyl, ethyl, propyl, isopropyl, butyl, isobutyl, tert-butyl, pentyl, hexyl, octyl, decyl or cyclohexyl;
an aryl radical having alkyl and other substituents on the aromatic ring, for example phenyl, methylphenyl, ethylphenyl, mesityl, cumyl, p-nitrophenylxylyl, hydroxyphenyl or naphthyl;

an aralkyl radical, for example benzyl, 1-phenylethyl, 2-phenylethyl, 2-phenylpropyl, cumylmethyl or mesitylmethyl;

an alkyloxy radical having from 1 to 10 carbon atoms and phosphorus or sulfur as a further heteroatom, for example methoxy, ethoxy, propyloxy, butyloxy, 2-ethylbutyloxy, 3-thiabutyloxy, 3-phosphabutyloxy;

an aralkyloxy radical having alkyl and heteroatom-containing substituents on the aromatic ring, for example benzyloxy, 1-phenylmethyloxy, (2-methyl)phenylmethoxy, p-sulfobenzyloxy or p-nitrobenzyloxy;

and where $R_{17}=R_{18}=R_{16}$, except when $R_{16}$ is H, where $R_{16}$, $R_{17}$ and $R_{18}$ may be identical or different and, when $R_{16}$ is H, $R_{17}$ and $R_{18}$ may be identical or different.

For the purposes of the present invention, acyloxylation refers to the introduction of an acyloxy radical of the formula —O—CO—R into an organic compound, as described, for example, by Römpp, 9th edition, 1995, page 47, preferably by addition of a carboxylic acid or a carboxylic acid derivative to the double bond of a fatty acid or fatty acid derivative.

Compounds of the general formula I may be prepared using compounds of the general formula II as double bond components

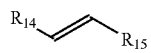

Formula II where $R_{14}$ is a carboxylic acid radical R—COOH where R is an alkyl, alkenyl, dienyl or polyenyl radical having from 2 to 20 carbon atoms and from 0 to 4 double bonds, preferably having from 3 to 11 carbon atoms and from 0 to 2 double bonds, for example, n-carboxyheptyl, n-carboxyundecyl, n-carboxy-4-heptenyl or esters thereof with monoalcohols, diols or polyols, such as methanol, ethanol, glycerol, pentaerythritol or trimethylolpropane;

and where $R_{15}$ is an alkyl, alkenyl, dienyl or polyenyl radical having from 2 to 20 carbon atoms and from 0 to 4 double bonds, preferably from 3 to 14 carbon atoms and from 0 to 3 double bonds, in particular from 3 to 10 carbon atoms and from 0 to 2 double bonds, for example, n-hexyl, n-octyl, 2-octenyl or 2,5-octadienyl.

Such double bond components may be represented by oleic acid, linoleic acid, linolenic acid, palmitoleic acid, eicosenoic acid and erucic acid and mixtures thereof, and by methyl oleate, methyl linoleate, methyl linolenate and methyl palmitoleate.

The double bond components used may also be glycerol trioleate, glycerol trilinolate, glycerol trilinoleate, trimethylolpropane trioleate, trimethylolpropane trilinolate, trimethylolpropane trilinoleate, pentaerythritol tetraoleate, pentaerythritol tetralinolate, pentaerythritol tetralinoleate or mixtures thereof or renewable raw materials such as rapeseed oil, sunflower oil, palm oil, coconut oil or olive oil.

The double bond components used may also be polyunsaturated fatty acids and/or fatty acid derivatives where a portion of the double bonds has first been hydrogenated and carboxylic acids and/or carbonyl halides and/or carboxylic anhydrides have then been added to the remaining double bonds.

To prepare the novel lubricants and pressure transfer media according to the invention, at least one double bond of the fatty acids and/or fatty acid derivatives and mixtures thereof should be acyloxylated using unbranched carboxylic acids of the formula IV,

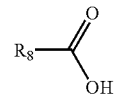

Formula IV where $R_8$ is H or a linear alkyl radical having from 2 to 16 carbon atoms, preferably from 2 to 4 carbon atoms, or an aromatic radical whose aromatic core may be substituted by alkyl groups and/or halogens such as F.

Other added carboxylic acids fall under the general formula III

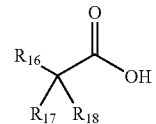

Formula III where $R_{16}$ is H or $R_{16}$ is an alkyl radical having from 1 to 10 carbon atoms, for example methyl, ethyl, propyl, isopropyl, butyl, isobutyl, tert-butyl, pentyl, hexyl, octyl, decyl or cyclohexyl;

an alkenyl radical having from 1 to 10 carbon atoms, for example ethenyl, n-propenyl, isopropenyl, hexenyl, 3-methylpentenyl or 3-ethylbutenyl;

an aryl radical having alkyl and other substituents on the aromatic ring, for example phenyl, methylphenyl, ethylphenyl, mesityl, cumyl, p-nitrophenylxylyl, hydroxyphenyl or naphthyl;

an aralkyl radical, for example benzyl, 1-phenylethyl, 2-phenylethyl, 2-phenylpropyl, cumylmethyl or mesitylmethyl;

an alkyloxy radical having from 1 to 10 carbon atoms and phosphorus or sulfur as a further heteroatom, for example methoxy, ethoxy, propyloxy, butyloxy, 2-ethylbutyloxy, 3-thiabutyloxy, 3-phosphabutyloxy;

an aralkyloxy radical having alkyl and heteroatom-containing substituents on the aromatic ring, for example benzyloxy, 1-phenylmethyloxy, (2-methyl)-phenylmethoxy, p-sulfobenzyloxy or p-nitrobenzyloxy;

and where $R_{17}=R_{18}=R_{16}$, except when $R_{16}$ is H, where $R_{16}$, $R_{17}$ and $R_{18}$ may be identical or different and, when $R_{16}$ is H, $R_{17}$ and $R_{18}$ may be identical or different.

Particular preference is given to adding neocarboxylic acids of the general formula V

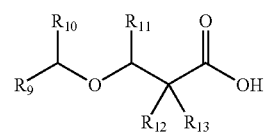

Formula V where $R_9$, $R_{10}$, $R_{12}$ and/or $R_{13}$ are identical or different and are hydrogen, straight-chain or branched alkyl, alkenyl or alkynyl radicals having up to 18 carbon atoms, cycloalkyl or cycloalkenyl radicals having from 5 to 8 carbon atoms, aryl, aralkyl or alkenylaryl radicals having from 6 to 16 carbon atoms or heterocyclic radicals, where each of the $R_9$ and $R_{10}$ and/or $R_{12}$ and $R_{13}$ radical pairs together with the carbon atom to which they are bonded may form a cycloalkane, cycloalkene or a heterocycle having from 5 to 7 ring members, and $R_9$, $R_{10}$, $R_{12}$ and $R_{13}$ may additionally carry substituents, in particular those which are inert under the reaction conditions, and $R_{11}$ is hydrogen or a straight-chain or branched alkyl radical.

Preference is given to carboxylic acids where $R_9$, $R_{10}$, $R_{12}$ and $R_{13}$ are identical or different and are hydrogen, straight-chain or branched alkyl radicals having from 1 to 12, in particular from 1 to 6 carbon atoms, alkenyl or alkynyl radicals having from 2 to 12, in particular from 2 to 6 carbon atoms. Preference is further given to compounds $R_9$, $R_{10}$, $R_{12}$ and $R_{13}$ are cycloalkyl or cycloalkenyl radicals having 5 or 6 carbon atoms, or are aryl, alkylaryl, aralkyl or alkenylaryl radicals having from 6 to 12 carbon atoms or are heterocyclic radicals which contain one or more nitrogen and/or oxygen and/or sulfur atoms. Furthermore, neocarboxylic acids are preferred where $R_{11}$ is hydrogen or a straight-chain or branched alkyl radical having from 1 to 12, in particular from 1 to 8, preferably from 1 to 4 carbon atoms. $R_{11}$ is particularly preferably hydrogen.

Examples of alkyl, alkenyl and alkynyl radicals include the methyl, ethyl, n-propyl, isopropyl, propenyl, isopropenyl, n-butyl, isobutyl, n-butenyl, i-butenyl, n-butynyl, pentyl, pentenyl, pentynyl, hexyl, hexenyl, heptyl, heptenyl, octyl, octenyl, nonyl, nonenyl, decyl, decenyl, dodecyl and dodecenyl radicals.

Representative examples of cycloalkyl radicals include cyclopentyl, cyclohexyl, cycloheptyl, cyclopentenyl and cyclohexenyl radicals.

Examples of useful aromatic radicals include the phenyl, benzyl, 2-phenylethyl, 2-phenylpropyl, 3-phenylpropyl, 2-phenylbutyl, 3-phenylbutyl and 4-phenylbutyl radicals.

Examples of heterocyclic radicals include furan, dihydrofuran, tetrahydrofuran, thiophene, dihydrothiophene, pyridine and thiopyran radicals.

The alkyl, cycloalkyl, aromatic and heterocyclic radicals may be substituted, in particular by radicals which are inert under the reaction conditions, such as halogen, alkoxy, carboxyl or carboxylate groups. However, it is not ruled out that in individual cases substituents are deliberately chosen which are changed in the course of the reaction, for example, formyl groups which are converted to formoxy radicals.

According to the invention, for example, the following novel carboxylic acids branched in the alpha-position to the carboxyl group may be used in this manner such as:

3-Propyloxy-2,2-dimethylpropionic acid

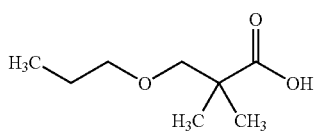

The spectroscopic data of this compound were determined as reported below.

| | |
|---|---|
| $^1$H-NMR | 0.89 ppm tr 3H, 1.19 ppm 2 6H, 3.42 ppm s 2H, 3.40 ppm s 2H, 1.56 ppm m 2H |
| $^{13}$C-NMR | 10.66 ppm $CH_3$, 23.06 ppm $CH_2$, 77.54 and 73.69 ppm O—$CH_2$, 43.83 ppm quaternary C, 22.46 ppm 2 $CH_3$, 183.01 ppm C=O |
| IR | 1706 cm$^{-1}$ C=O, 2976, 2935, 2879 cm$^{-1}$ $v_{s,as}$ $CH_2$, $CH_3$, broad shoulder at 2700–2500 cm$^{-1}$ |
| MS | m/z: 175 (M$^+$.), 131, 115, 101, 102, 87, 83 |

3-Butyloxy-2,2-dimethylpropionic acid

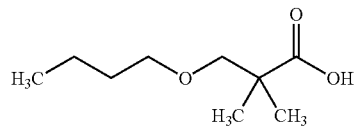

The following spectroscopic data were determined:

| | |
|---|---|
| $^1$H-NMR | 0.90 ppm tr 3H, 1.34 ppm m 2H, 1.53 ppm q 2H, 3.45 ppm tr 2H, 3.42 ppm s 2H, 1.19 ppm s 6H |
| $^{13}$C-NMR | 14.01 ppm $CH_3$, 19.69 ppm $CH_2$, 31.95 ppm $CH_2$, 77.65 and 71.80 ppm O—$CH_2$, 43.87 ppm quaternary C, 22.44 ppm 2 $CH_3$, 183.72 ppm C=O |
| IR | 1706 cm$^{-1}$ C=O, 2971, 2935, 2879 cm$^{-1}$ $v_{s,as}$ $CH_2$, $CH_3$ broad shoulder at 2700–2500 cm$^{-1}$ |
| MS | m/z 189 (M$^+$.), 131, 114, 102, 101, 87, 73 |

3-Isobutoxy-2,2-dimethylpropionic acid

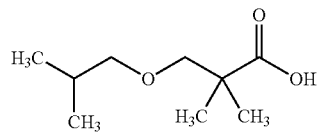

The following spectroscopic data were determined for this compound:

| | |
|---|---|
| $^1$H-NMR | 0.88 ppm s 3H, 0.89 ppm s 3H, 1.84 ppm m 1H, 3.20 ppm d 2H, 3.41 ppm s 2H, 1.20 ppm 2 6H |
| $^{13}$C-NMR | 19.36 ppm 2 $CH_3$, 28.70 ppm CH, 78.83 and 77.75 ppm O—$CH_2$, 22.44 ppm 2 $CH_3$, 43.87 ppm quaternary C, 183.04 ppm C=O |
| IR | 1706 cm$^{-1}$ C=O, 2976, 2935, 2868 cm$^{-1}$ $v_{s,as}$ $CH_2$, $CH_3$, broad shoulder at 2700–2500 cm$^{-1}$ |
| MS | m/z: 189 (M$^+$.), 131, 115, 102, 101, 87, 73 |

3-(2-Ethylbutyloxy)-2,2-dimethylpropionic acid

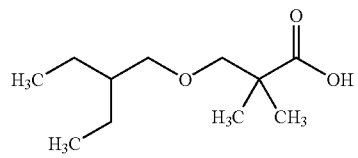

For this compound, the following spectroscopic data were measured:

| | |
|---|---|
| $^1$H-NMR | 0.93 ppm tr 3H, 0.86 ppm tr 3H, 1.59 ppm m 4H, 2.22 ppm m 1H, 3.33 ppm d 2H, 3.40 ppm s 2H, 1.19 ppm s 6H |
| $^{13}$C-NNR | 11.87 and 11.26 ppm $CH_3$, 23.86 and 25.16 ppm $CH_2$, 49.34 ppm CH, 77.92 and 74.36 ppm O—$CH_2$, 22.46 ppm 2 $CH_3$, 43.90 ppm quaternary C, 183.16 ppm C=O |
| IR | 1706 cm$^{-1}$ C=O, 2966, 2935, 2879 cm$^{-1}$ $v_{s,as}$ $CH_2$, $CH_3$ broad shoulder at 2700–2500 cm$^{-1}$ |
| MS | m/z: 217 (M$^+$.), 185, 145, 133, 131, 115, 102, 101, 85, 73 |

3-Benzyloxy-2,2-dimethylpropionic acid

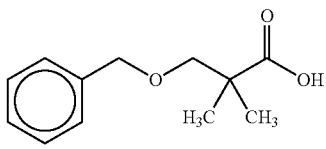

The compound has the following spectroscopic data:

| | |
|---|---|
| $^1$H-NNR | 7.20 ppm m 5H, 4.37 ppm s 2H, 3.35 ppm s 2H, 1.08 ppm s 6H |
| $^{13}$C-NMR | 125–130 ppm aromatic C, 77.13 and 73.28 ppm O—$CH_2$, 21.87 ppm 2 $CH_3$, 43.80 ppm quaternary C, 182.89 ppm C=O |
| IR | 1701 cm$^{-1}$ C=O, 3094, 3063, 3033 cm$^{-1}$ $v_{ar}$ CH, 2984, 2909, 2878 cm$^{-1}$ $v_{s,as}$ $CH_2$, $CH_3$, broad shoulder at 2700–2500 cm$^{-1}$ |
| MS | m/z: 222 (M$^+$.), 191, 116, 107, 101, 91, 65 |

3-(2-Methylphenyloxy)-2,2-dimethylpropionic acid

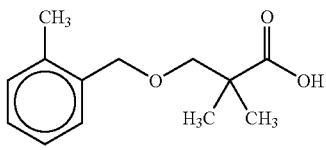

The compound gave the following spectroscopic data:

| | |
|---|---|
| $^1$H-NMR | 7.0–7.3 ppm m 4H, 2.28 ppm s 3H, 3.48 ppm s 2H, 3.44 ppm s 2H, 1.21 ppm s 6H |
| $^{13}$C-NMR | 125–130 ppm aromatic C, 77.31 and 72.28 ppm O—$CH_2$, 43.78 ppm quaternary C, 22.46 ppm $CH_3$—ar, 18.82 and 15.32 ppm $CH_3$, 182.79 ppm C=O |
| IR | 1703 cm$^{-1}$ C=O, 3073, 3027 cm$^{-1}$ $v_{ar}$ CH, 2976, 2935, 2868 cm$^{-1}$ $v_{s,as}$ $CH_2$, $CH_3$, broad shoulder at 2700–2500 cm$^{-1}$ |
| MS | m/z: 237 (M$^+$.), 209, 193, 145, 131, 121, 115, 105 |

The carboxylic acids mentioned above are obtained by catalytic gas phase isomerization of appropriately substituted 1,3-dioxanes to give aldehydes and the subsequent oxidation thereof to the carboxylic acids. The conversion of 1,3-dioxanes to aldehydes is described in EP-A-0 199 210.

The isomerization catalysts used are acidic solids. These include metal oxides such as $Al_2O_3$, $TiO_2$, $SiO_2$, $ZrO_2$, $Nb_2O_5$ or phosphates such as boron phosphate, aluminum phosphate or iron phosphate or sulfated zirconium dioxide or titanium dioxide, but also ion exchange resins such as Amberlyst, Nafion and Nafion/silica composites.

Catalysts used for the oxidation of the aldehydes obtained by isomerization of the dioxanes are advantageously metals or transition groups I and VIII of the Periodic Table in metallic form or in the form of their oxides. These catalysts may be used pure or supported. Preference is given to using silver, which is used on supports, or silver(I) oxide, which is used in pure form.

To prepare the novel lubricants and pressure transfer media according to the invention, the double bonds of the natural fatty acids, natural fatty acid derivatives and mixtures thereof may be acyloxylated not with carboxylic acids, but instead with the corresponding carboxylic anhydrides and/or carbonyl halides. The fatty acids or fatty acid derivatives used may be of natural or synthetic origin. In the case of certain carboxylic acid component, the use of further solvents in the acyloxylation may be unnecessary, and instead the carboxylic acid component itself may be used as solvent in a molar excess in the range from 1.2 to 150 mol %.

The reactions are carried out in the presence of homogeneous or heterogeneous catalysts. It was shown that the use of homogeneous or heterogeneous acid catalysts gives good conversions and high selectivities in the addition reaction.

According to the invention, heterogeneous catalysts such as zeolites, solid phosphoric acid, phosphates of aluminum, boron, iron, strontium, cerium and zirconium, oxides such as $Al_2O_3$, $SiO_2$, $B_2O_3$, $Fe_2O_3$, $ZrO_2$, $SnO_2$ and $GeO_2$ and organic ion exchangers such as Amberlyst or Nafion, which are easily removed from the products formed, are particularly advantageous. The use of zeolites as heterogeneous catalysts is known [H. Kessler, *Comprehensive Supramolecular Chemistry Volume 7: Solid-state Supramolecular Chemistry: Two- and Three-dimensional inorganic Network* 1996, pp. 425–464; L. B. McCusker, *Comprehensive Supramolecular Chemistry Volume 7: Solid-state Supramolecular Chemistry: Two- and Three-dimensional Inorganic Network* 1996, pp. 393–424], and likewise the use of aluminum phosphates [E. M. Flanigen, B. M. Lok, R. L. Patton, S. T. Wilson in Y. Murakami, A. Ijima and J. W. Ward (Eds.), *New Developments in Zeolite Science and Technology, Proc. 7$^{th}$ Intl Zeolite Conf.*, Tokyo, 1986, Kodansha Ltd. Tokyo and Elsevier, Amsterdam, pp. 101–112]. Nafion/silica composite materials in particular deliver good results. In this case, it is advantageous to dry the catalyst before use in the reaction for more than one hour at elevated temperature under reduced pressure. The heterogeneous catalysts mentioned are easy to regenerate and may accordingly be used repeatedly in the process which is particularly advantageous from a technical point of view. While formic acid also adds to the double bond of natural fatty acids and fatty acid derivatives without catalyst, the use of higher carboxylic acids in the absence of catalysts gives no or only very low conversion, although the reaction with carboxylic acids may in individual cases also proceed autocatalytically.

Useful homogeneous acid catalysts include, inter alia, $H_2SO_4$, methylsulfonic acid, $H_3PO_4$ and derivatives thereof, $H_3BO_3$, $HNO_3$, HCl, HF, $HFBF_3$, $AlCl_3$, $FeCl_3$, $SnCl_2$, $AlBr_3$ and $FeBr_3$.

According to the invention, novel esters of natural fatty acids and fatty acid derivatives may be prepared according to the following equation 1 or equation 2:

Equation 1

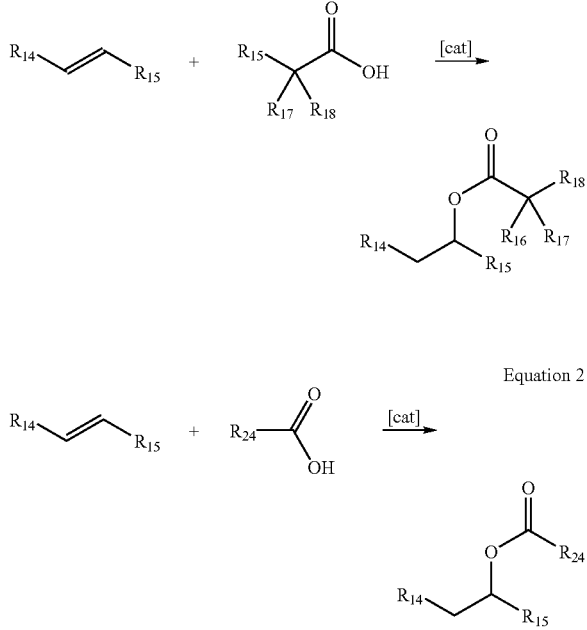

Equation 2

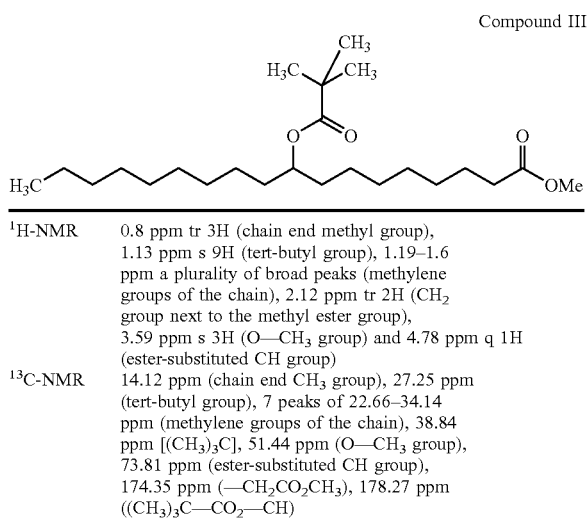

The analysis was carried out by HPLC (high pressure liquid chromatography) and GC (gas chromatography). Additional information on the identity of the products prepared was obtained by mass spectrometry (MS). The addition products formed may be separated from their starting products by distillation or column chromatography and isolated in a purity in the range from 70 to 99% and then characterized by NMR and IR spectroscopy.

For example, the ester having the following chemical formula (compound III) has the following characteristic features:

Compound III

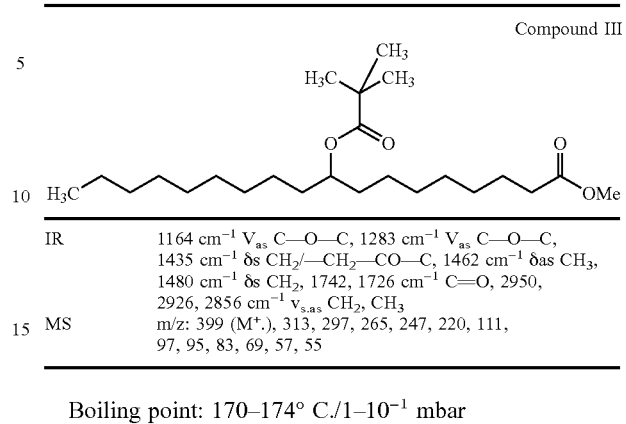

| $^1$H-NMR | 0.8 ppm tr 3H (chain end methyl group), 1.13 ppm s 9H (tert-butyl group), 1.19–1.6 ppm a plurality of broad peaks (methylene groups of the chain), 2.12 ppm tr 2H (CH$_2$ group next to the methyl ester group), 3.59 ppm s 3H (O—CH$_3$ group) and 4.78 ppm q 1H (ester-substituted CH group) |
|---|---|
| $^{13}$C-NMR | 14.12 ppm (chain end CH$_3$ group), 27.25 ppm (tert-butyl group), 7 peaks of 22.66–34.14 ppm (methylene groups of the chain), 38.84 ppm [(CH$_3$)$_3$C], 51.44 ppm (O—CH$_3$ group), 73.81 ppm (ester-substituted CH group), 174.35 ppm (—CH$_2$CO$_2$CH$_3$), 178.27 ppm ((CH$_3$)$_3$C—CO$_2$—CH) |
| IR | 1164 cm$^{-1}$ $V_{as}$ C—O—C, 1283 cm$^{-1}$ $V_{as}$ C—O—C, 1435 cm$^{-1}$ δs CH$_2$/—CH$_2$—CO—C, 1462 cm$^{-1}$ δas CH$_3$, 1480 cm$^{-1}$ δs CH$_2$, 1742, 1726 cm$^{-1}$ C=O, 2950, 2926, 2856 cm$^{-1}$ $v_{s,as}$ CH$_2$, CH$_3$ |
| MS | m/z: 399 (M$^+$.), 313, 297, 265, 247, 220, 111, 97, 95, 83, 69, 57, 55 |

Boiling point: 170–174° C./1–10$^{-1}$ mbar

| Elemental analysis: | C$_{found}$: 72.4% | C$_{calculated}$: 72.3% |
|---|---|---|
| | H$_{found}$: 12.0% | H$_{calculated}$: 11.6% |

According to the invention, it is advantageous for ester formation to use the carboxylic acid and/or the carboxylic anhydride and/or the carbonyl halides in excess and as the solvent to avoid the use of additional solvents.

The carboxylic acid is added to the double bonds of the oleochemical component. The carbenium ion mechanism may lead to a small extent to double bond isomerization. Reaction by-products may include polymers and to a small extent transesterification products by cleavage of the fatty acid ester and esterification of the carboxylic acid component present in excess.

After the end of the reaction, the heterogeneous catalysts can be easily filtered off, washed and regenerated to restore the starting activity.

Unreacted carboxylic acids or derivatives thereof, like the oil component, may be distillatively or chromatographically removed from the product formed. Likewise, the addition products formed may be isolated by distillation or column chromatography in a purity of from 70 to 99% and characterized spectroscopically by NMR and IR.

The carboxylic acid or derivatives thereof are added to the natural fatty acids and natural fatty acid derivatives in the liquid phase and at temperatures in the range from 0 to 400° C., preferably from 25 to 250° C., in particular from 70 to 180° C. The reaction is carried out at pressures in the range from 1000 to 10,000 hPa, preferably from 1000 to 5000 hPa, in particular from 1000 to 2000 hPa. Catalyst space velocities of from 0.001 mmol to 50 mol of reactant per gram of catalyst are used, preferably from 0.01 mmol to 30 mol, in particular from 0.1 to 10 mol.

The reaction time is in the range from one minute to 12 days, preferably in the range from 10 minutes to 5 days, in particular from one hour to 48 hours. The molar excess of the acid component compared to the oil component is from 0.3 to 300, preferably from 1.2 to 150, in particular from 10 to 80.

Higher branching of the carboxylic acid or carboxylic acid derivative added normally reduces their reactivity. However, the selectivity of the reaction is at the same time distinctly increased, since the lower acid strength results in fewer side reactions such as polymerization and transesterification. When the reaction is scaled up, the good selectivities and conversions can be retained, but longer reaction times are sometimes required.

The reaction may be carried out in a batchwise or continuous process. Thus a batchwise process at atmospheric pressure may employ stirred tank reactors; when working under pressure, stainless steel autoclaves may be used. In the semicontinuous method, stirred tank batteries are used. In the continuous reaction procedure, preference is given to using tubular reactors with fixed catalyst beds. Loop and fluidized bed reactors may also be used.

To carry out the reaction, the acid component is added to the natural fatty acids or natural fatty acid derivatives used as the reactant in the presence of the catalyst at ambient temperature with stirring and the flask is introduced into a heating bath of the desired reaction temperature. The reaction is effected by means of stirring and cooling by means of a reflux condenser. Analysis is effected by withdrawing a defined sample quantity at different time intervals and analyzing it by means of HPLC or GC. After the end of the reaction, the catalyst is filtered off, washed with an organic solvent and regenerated using hydrochloric or nitric acid. Regeneration may also be effected under an oxygen atmosphere by burning off carbon deposits (zeolites). The reaction mixture is fractionated by high vacuum distillation or column chromatography and remaining oil and acid components are recycled into the reaction.

The oil component used may be modified by preceding partial hydrogenation.

To this end, the natural fatty acids or natural fatty acid derivatives may be reacted under elevated pressure with hydrogen over various heterogeneous catalysts, for example, nickel, platinum or palladium on support materials, at temperatures of around 150° C. in the liquid phase. Carboxylic acids can be catalytically added to the remaining double bonds according to the above description.

The novel lubricants and pressure transfer media according to the invention have high oxidation and hydrolysis stability, improved viscosity properties with a wide viscosity range, low vapor pressure and optimized lubricant film formation and also reduced frictional moments, for example in a spindle bearing. They have good biodegradability. The substances or substance mixtures according to the invention may also find use as functional liquids and lubricant additives.

The invention will now be more particularly described with reference to illustrative examples.

EXAMPLES

Catalyst A

Catalyst A=®Nafion SAC 13, i.e. Nafion/silica composite material having a Nafion content of 13%. Nafion is a registered trademark of DuPont. It is a perfluorinated polymer which is obtained by sulfonation of super acid functions. Coprecipitation of Nafion with silica gel gives materials having varying Nafion contents and a surface area of from 300 to 400 m²/g, which are referred to as Nafion composites.

Catalyst B

Catalyst B=®Amberlyst 15 from Fluka having a surface area of 45 m²/g and a porosity of 32%. Amberlyst is a trademark of Rohm and Haas Company. Macroreticular ion exchangers are prepared by copolymerization of styrene with from 3 to 5% of divinylbenzene for crosslinking. The acid function is formed by $SO_3H$ groups.

Examples 1 and 2

Formic Acid without Catalyst 190 g of methyl oleate were reacted with 600 g of formic acid with stirring using a magnetic stirrer bar at a temperature of 120° C. Stirring was effected for 18 h under reflux. After the reaction, a sample was taken and analyzed by gas chromatography using a 60 m Chrompack SE-54 column.

The reaction proceeded according to the following equation (3):

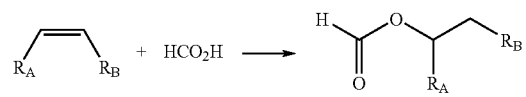

$R_A$: $H_3C$—$(CH_2)_6$—$CH_2$—   $R_B$: —$(CH_2)_7CO_2CH_3$

| Example | Reaction time [h] | Molar ratio: * | C [%] | S [%] | Y [%] |
|---|---|---|---|---|---|
| 1 | 18 | 20 | 72.5 | 96.5 | 70.0 |
| 2 | 18 | 26 | 85.5 | 91.1 | 77.9 |

* expressed as formic acid/methyl oleate

The reaction mixture was fractionated under high vacuum. Formic acid came over at 54° C./150 torr, methyl oleate and remaining reactant components at 133° C./1·10⁻¹ mbar and methyl 9(10)-formyloxystearate at 160–174° C./1·10⁻¹ mbar. 105 g of product mixture having a methyl 9(10)-formyloxystearate content of 90% were obtained.

Characterization of compound I=methyl 9(10)-formyloxystearate:

| | |
|---|---|
| ¹H-NMR | 0.83 ppm tr 3H (chain end methyl group), 1.19–1.6 ppm a plurality of broad peaks (chain methylene groups), 2.25 ppm tr 2H (CH₂ group next to the methyl ester group), 3.61 ppm s 3H (O—CH₃ group), 4.78 ppm q 1H (ester-substituted CH group), 8.04 ppm s 1H (formyloxy group) |
| ¹³C-NMR | 14.13 ppm (chain end CH₃ group), 7 peaks of 22.70–34.09 ppm (methylene groups of the chain), 51.44 ppm (O—CH₃ group), 74.53 ppm (ester-substituted CH group), 161.14 ppm (HCO₂OH), 174.31 ppm (—CH₂—CO₂—CH₃) |
| IR | 1183 cm⁻¹ $v_{as}$ C—O—C (strong peak for formates), 1377 cm⁻¹ δs CH₃, 1437 cm⁻¹ δs CH₂/—CH₂—CO—C, 1465 cm⁻¹ δas CH₃, 1377 cm⁻¹ δs CH₂, 1742, 1725 cm⁻¹ C=O, 2928, 2856 cm⁻¹ $v_{s,as}$ CH₂, CH₃ |
| MS | m/z: 343 (M⁺.), 313, 297, 265, 264, 246, 235, 222, 111, 109, 81, 67, 55 |

Boiling point: 160–174° C./1·10⁻¹ mbar

| Elemental analysis: | $C_{found}$: 70.4% | $C_{calculated}$: 70.13% |
|---|---|---|
| | $H_{found}$: 11.38% | $H_{calculated}$: 11.18% |

Example 3

Formic Acid with Amberlyst as Catalyst

| | | |
|---|---|---|
| Methyl oleate: | 2.5 g | |
| Formic acid: | 19.55 g | |
| Catalyst: | 2.5 g | |
| Temperature: | 120° C. | |

| Example | Catalyst | Reaction time [h] | C [%] | S [%] | Y [%] |
|---|---|---|---|---|---|
| 3 | Amberlyst 15 | 8 | 99.9 | 80.8 | 80.8 |

Example 4

Formic Acid with Nafion/Silica Composite SAC 13 as Catalyst

| Example | Catalyst | Reaction time [h] | C [%] | S [%] | Y [%] |
|---|---|---|---|---|---|
| 4 | Nafion SAC 13 | 8 | 83.0 | 77.3 | 64.1 |

Example 5

Acetic Acid with Sulfuric Acid as Catalyst

| | | |
|---|---|---|
| Methyl oleate: | 2.5 g | |
| Acetic acid: | 25.5 g | |
| Catalyst: | 2.5 g | |
| Temperature: | 120° C. | |

| Example | Catalyst | Reaction time [h] | C [%] | S [%] | Y [%] |
|---|---|---|---|---|---|
| 5 | $H_2SO_4$ | 20 | 90.1 | 40.5 | 36.5 |

Example 6

Acetic Acid with Phosphoric Acid on Silica as Catalyst

| Example | Catalyst | Reaction time [h] | C [%] | S [%] | Y [%] |
|---|---|---|---|---|---|
| 6 | $H_3PO_4$ on $SiO_2$ | 24 | 80.4 | 51.4 | 41.4 |

Example 7

Acetic Acid Using Nafion/Silica Composite SAC 13 as Catalyst

| Example | Catalyst | Reaction time [h] | C [%] | S [%] | Y [%] |
|---|---|---|---|---|---|
| 8 | Nafion SAC 13 | 32 | 55.2 | 4 | 51.8 |

Analysis of methyl acetoxystearate

Characterization of compound II. Methyl 9(10)-acetoxystearate

| | |
|---|---|
| $^1$H-NMR | 0.81 ppm tr 3H (chain end methyl group), 1.19–1.6 ppm a plurality of broad peaks (chain methylene groups), 1.97 ppm s 3H ($CH_3$ group acetoxy group), 2.27 ppm tr 2H ($CH_2$ group next to the methyl ester group), 3.60 ppm s 3H (O—$CH_3$ group), 4.78 ppm q 1H (ester-substituted CH group) |
| $^{13}$C-NMR | 14.15 ppm (chain end $CH_3$ group), 21.34 ppm ($CH_3$ group acetoxy group), peaks of 22.73 to 34.17 ppm (chain methylene groups), 74.53 ppm (ester-substituted CH group), 174.13 ppm ($CH_2CO_2CH$), 179.97 ppm ($CH_3C$—$CO_2$—CH) |
| IR | 1164 $cm^{-1}$ $v_{as}$ C—O—C, 1283 $cm^{-1}$ $v_{as}$ C—O—C, 1361 $cm^{-1}$ δs $CH_3/CH_3$—$CO_2$—, 1435 $cm^{-1}$ δs $CH_2/$—$CH_2$—CO—C, 1462 $cm^{-1}$ δas $CH_3$, 1481 $cm^{-1}$ δs $CH_2$, 1745, 1726 $cm^{-1}$ C=O, 2926, 2856 $cm^{-1}$ $v_{s,as}$ $CH_2$, $CH_3$ |
| MS | m/z: 356 (M$^+$.), 355, 313, 295, 281, 263, 245, 187, 155, 109, 95, 81, 67, 55 |

Boiling point: 170–182° C./5·10$^{-2}$ mbar

Example 8

30 g of Nafion SAC 13 were dried under high vacuum at a temperature of 100° C. over a period of four hours, then introduced into a 2 l one-neck flask and admixed with 100 g of a fatty acid methyl ester mixture having a methyl oleate content of 66%. 570 g of pivalic acid were added with stirring using a magnetic stirrer bar, then the flask was introduced into an oil bath heated to 120° C. Over a period of 15 h, the mixture was stirred with cooling by a reflux condenser. After the end of the reaction, a sample was taken and analyzed by gas chromatography using a 60 m Chrompack SE-54 column. A conversion of methyl oleate of 45% at a selectivity for the addition product of 96% was determined.

The reaction proceeds according to equation (4):

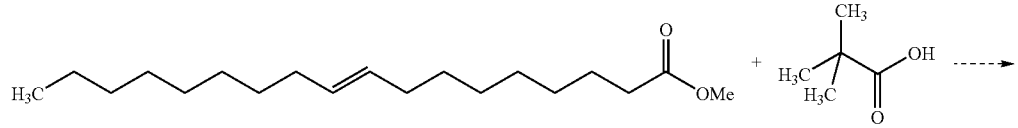

-continued

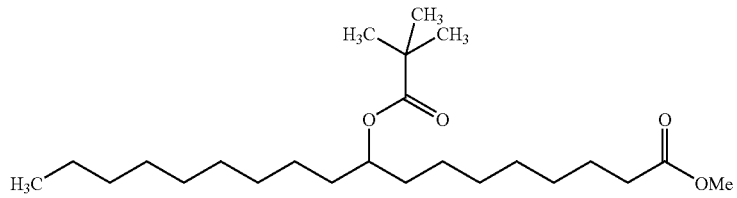

The catalyst was then filtered off and freed of reaction mixture residues by washing with acetone. The acetone was then distilled off at atmospheric pressure and the remaining residue united with the reaction mixture. If the catalyst should be deactivated after such a reaction, it is regenerated by treatment with hydrochloric acid.

The reaction mixture was then fractionated under high vacuum. Pivalic acid came over at 82° C./25 torr, methyl oleate and the remaining reactant components at 133° C./1·10$^{-1}$ mbar and methyl 9-(10)-[2,2-dimethylpropionyloxy]stearate at from 170 to 174° C./1·10$^{-1}$ mbar. 30 g of product mixture having a methyl 9-(10)-[dimethylpropionyloxy]stearate content of 70% are obtained.

Characterization of compound III: methyl 9-(10)-[2,2'-dimethylpropionyloxy]stearate

| | |
|---|---|
| $^1$H-NMR | 0.8 ppm tr 3H (chain end methyl group), 1.13 ppm s 9H (tert-butyl group), 1.19–1.6 ppm a plurality of broad peaks (chain methylene groups), 2.12 ppm tr 2H (CH$_2$ group next to the methyl ester group), 3.59 ppm s 3H (O—CH$_3$ group), 4.78 ppm q 1H (ester-substituted CH group) |
| $^{13}$C-NMR | 14.12 ppm (chain end CH$_3$ group), 27.25 ppm (tert-butyl group), 7 peaks of 22.66 to 34.14 ppm (chain methylene groups), 38.84 ppm {(CH$_3$)$_3$C}, 51.44 ppm (O—CH$_3$ group), 73.81 ppm (ester-substituted CH group), 174.35 ppm (—CH$_2$CO$_2$CH$_3$), 178.27 ppm {(CH$_3$)$_3$C—CO$_2$—CH} |
| IR | 1164 cm$^{-1}$ $v_{as}$ C—O—C, 1283 cm$^{-1}$ $v_{as}$ C—O—C—, 1435 cm$^{-1}$ δs CH$_2$/—CH$_2$—CO—C, 1462 cm$^{-1}$ δas CH$_3$, 1480 cm$^{-1}$ δs CH$_2$, 1742, 1726 cm$^{-1}$ C=O, 2950, 2926, 2856 cm$^{-1}$ $v_{s,as}$ CH$_2$, CH$_3$ |
| MS | m/z: 399 (M$^+$.), 313, 297, 265, 247, 220, 111, 97, 95, 83, 69, 57, 55 |

Boiling point: 170–174° C./1·10$^{-1}$ mbar

| Elemental analysis: | C$_{found}$: 72.4% | C$_{calculated}$: 72.3% |
|---|---|---|
| | H$_{found}$: 12.0% | H$_{calculated}$: 11.6% |

Examples 9 and 10

Examples 9 and 10 illustrate a comparison of the catalysts Nafion SAC 13 (A) and Amberlyst 15 (B) in the addition of pivalic acid to the double bond of methyl oleate. The reaction parameters were: catalyst velocity 4 mmol/g of catalyst, molar excess of pivalic acid compared to methyl oleate=25, temperature 120° C., reaction time 8 hours, batch reaction under atmospheric pressure; catalysts used without preceding drying.

| Example | Catalyst | Methyl oleate conversion [%] | Selectivity for compound III [%] | Yield of compound III [%] |
|---|---|---|---|---|
| 9 | A | 32 | 98 | 31 |
| 10 | B | 22 | 50 | 11 |

Examples 11 to 13

Examples 11 to 13 show a comparison of different Y-zeolites as heterogeneous catalysts in the addition of pivalic acid to the double bond of methyl oleate. The reaction parameters were: catalyst velocity 4 mmol/g of catalyst, molar excess of pivalic acid compared to methyl oleate=25, temperature 120° C., reaction time 48 h, batch reaction under atmospheric pressure, catalysts used after preceding calcining at 550° C. for 12 hours

| Catalyst number | Manufacturer and reference | SiO$_2$/Al$_2$O$_3$ modulus |
|---|---|---|
| 7 | Valor CBV-730 | 22 |
| 9 | CBV-780SDUS | 28 |
| 32 | CBU-780 | 24 |

| Example | Catalyst | Methyl oleate conversion | Selectivity for compound III [%] | Yield of compound III [%] |
|---|---|---|---|---|
| 11 | 7 | 45.6 | 91.0 | 41.5 |
| 12 | 9 | 33.5 | 92.2 | 30.9 |
| 13 | 32 | 34.3 | 93 | 31.9 |

Examples 14 and 15

Example 14 shows the reproducibility of the results with the Y-zeolite which corresponds to catalyst 7. Example 15 showed that the Y-zeolite after calcining can be used repeatedly without, as is observed for catalyst 32, losing activity. In both examples, the addition of pivalic acid to the double bond of methyl oleate was carried out as in examples 11 to 13. The reaction parameters were catalyst velocity 4 mmol/g of catalyst, molar excess of pivalic acid compared to methyl oleate=25, temperature 120° C., reaction time: 48 h, batch reaction under atmospheric pressure; catalysts used after preceding calcining at 550° C. for 12 hours.

| Example | Catalyst | Methyl oleate conversion [%] | Selectivity for compound III [%] | Yield of compound III [%] |
|---|---|---|---|---|
| 14 | 7 | 46.7 | 91.9 | 42.9 |
| 15 | 32 | 40.4 | 90.8 | 36.7 |

Examples 16 to 18

Examples 16 to 18 illustrate the effect of a higher degree of branching of the added carboxylic acid on conversion and selectivity. The starting materials were methyl oleate, Nafion SAC 13 catalyst, a molar excess of carboxylic acid compared to methyl oleate=50 (pivalic acid=25), temperature 120° C., reaction time 8 h, batch reaction under atmospheric pressure; catalyst used without preceding drying.

| Example | Carboxylic acid used | Methyl oleate conversion [%] | Selectivity for stearic acid adduct [%] | Yield of stearic acid adduct [%] |
|---|---|---|---|---|
| 16 | Formic acid | 83 | 77 | 64 |
| 17 | Acetic acid | 47 | 83 | 39 |
| 18 | Pivalic acid | 32 | 98 | 31 |

Examples 19 and 20

Examples 19 and 20 show the scale-up of the addition of pivalic acid to the double bond of methyl oleate. The catalyst was Nafion SAC 13, and the reaction parameters were: catalyst velocity 4 mmol/g of catalyst, molar excess of pivalic acid compared to methyl oleate=25, temperature 120° C., batch reaction under atmospheric pressure; catalysts used without preceding drying.

| Example | Quantity of methyl oleate used [g] | Reaction time [h] | Conversion of methyl oleate [%] | Selectivity of compound III [%] | Yield of compound III [%] |
|---|---|---|---|---|---|
| 19 | 1 | 8 | 29 | 88 | 26 |
| 20 | 100 | 15 | 32 | 98 | 31 |

Examples 21 to 25

Examples 21 to 25 illustrate the behavior of the reaction system when Nafion SAC 13 is pretreated, reused and regenerated in the addition of pivalic acid to the double bond of methyl oleate. The reaction conditions were: catalyst velocity 4 mmol/g of catalyst, molar excess of pivalic acid compared to methyl oleate=25, temperature 120° C., batch reaction under atmospheric pressure, reaction time 15 h.

| Example | Catalyst treatment | Conversion of methyl oleate [%] | Selectivity of compound III [%] | Yield of compound III [%] |
|---|---|---|---|---|
| 21 | Untreated | 29 | 88 | 26 |
| 22 | Dried under high vacuum at 20° C. for 24 h | 45 | 96 | 44 |
| 23 | 2nd use, washed with acetone and dried | 36 | 89 | 32 |
| 24 | 3rd use, washed with acetone and dried | 33 | 97 | 32 |
| 25 | Used, washed with acetone and regenerated with HCl, dried | 41 | 91 | 38 |

Example 26

In a further experiment, 3-benzyloxy-2,2-dimethylpropionic acid was used as the acid component.

3-Benzyloxy-2,2-dimethylpropionic acid

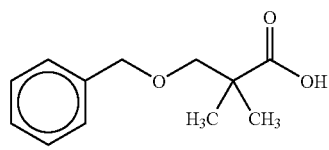

The spectroscopic data of the compound have already been reported further back in the text. Nafion SAC 13 was used as catalyst for acyloxylating methyl oleate. The following reaction conditions were selected: catalyst velocity 4 mmol/g of catalyst, molar excess of pivalic acid compared to methyl oleate=25, temperature 120° C., batch reaction under atmospheric pressure, reaction time 24 h.

| Example | Catalyst treatment | Conversion of methyl oleate [%] | Selectivity for target compound [%] | Yield of target compound [%] |
|---|---|---|---|---|
| 26 | Dried under high vacuum at 20° C. for 24 h | 26.5 | 36.3 | 9.6 |

Example 27

Example 27 illustrates the properties of the methyl formyloxystearate and methyl [2,2-dimethylpropionyloxy]-stearate esters prepared according to examples 1 and 4 compared to pure methyl oleate (base raw material).

| | Methyl oleate | Methyl formyl-oxystearate | Methyl [2,2-dimethyl-propionyloxy] stearate |
|---|---|---|---|
| KV (40° C.) [mm²/s] | 4.5 | 12.0 | 13.1 |
| KV (100° C.) [mm²/s] | 1.7 | 3.1 | 3.4 |
| VI | 178 | 120 | 139 |
| ROBOT[1] [min] | 10 | 165 | 27 |

| | Methyl oleate | Methyl formyl-oxystearate | Methyl [2,2-dimethyl-propionyloxy] stearate |
|---|---|---|---|
| Pour point [° C.] | −18 | −18 | −9 |
| Boiling point [° C.] | 133/ $10^{-1}$ mbar | 160–174/ $10^{-1}$ mbar | 170–174/ $10^{-1}$ mbar |
| Density (15° C.) [kg/m$^3$] | | 933.65 | 902.73 |

[1)]Conditions: 35 g of lubricant; 6.25 bar of oxygen; T = 120° C., without catalyst Further Examples Further useful branched carboxylic acids for addition to the double bonds of natural fatty acids and natural fatty acid derivatives include, for example, the following carboxylic acids whose spectroscopic properties have already been reported individually in the description:

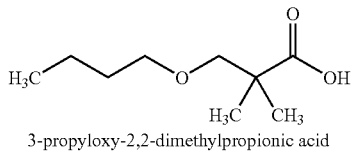
3-propyloxy-2,2-dimethylpropionic acid

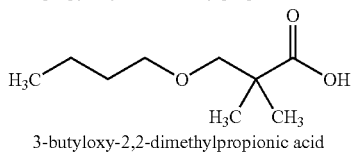
3-butyloxy-2,2-dimethylpropionic acid

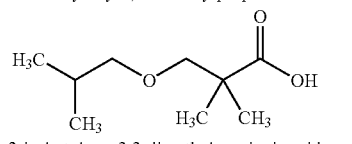
3-isobutyloxy-2,2-dimethylpropionic acid

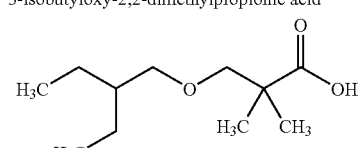
3-(2-ethylbutyloxy)-2,2-dimethylpropionic acid
and

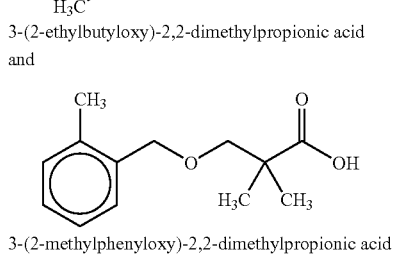
3-(2-methylphenyloxy)-2,2-dimethylpropionic acid

The invention claimed is:

1. A lubricant or a pressure transfer medium, comprising, in a medium suitable for a lubricant or a pressure transfer medium, one or more fatty acids and/or fatty acid derivatives obtainable by acyloxylation of at least one double bond.

2. The lubricant or the pressure transfer medium, as claimed in claim 1, wherein the at least one double bond is acyloxylated by one or more carboxylic acid radicals.

3. The lubricant or the pressure transfer medium, as claimed in claim 1, wherein the at least one double bond of the one or more fatty acids and/or fatty acid derivatives is acyloxylated by at least one unbranched carboxylic acid of the chemical formula IV:

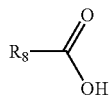

Formula IV wherein $R_8$ is H or a linear alkyl radical having from 2 to 16 carbon atoms, or an aromatic radical whose aromatic core may be substituted by one or more alkyl groups and/or halogens.

4. The lubricant or the pressure transfer medium, as claimed in claim 1, comprising one or more fatty acids and/or fatty acid derivatives of the formula I

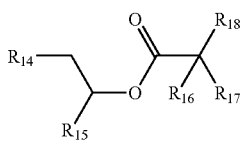

Formula I wherein $R_{14}$ is a carboxylic acid radical R—COOH wherein R is an alkyl, alkenyl, dienyl or polyenyl radical having from 2 to 20 carbon atoms and from 0 to 4 double bonds, $R_{15}$ is an alkyl, alkenyl, dienyl or polyenyl radical having from 2 to 20 carbon atoms and from 0 to 4 double bonds, R16 is H, an alkyl radical having from 1 to 10 carbon atoms, an aryl radical having an alkyl and other substituents on the aromatic ring, an aralkyl radical, an alkyloxy radical having from 1 to 10 carbon atoms optionally comprising phosphorus or sulfur as a further heteroatom, or an aralkyloxy radical optionally having alkyl and/or heteroatom-containing substituents on the aromatic ring, and $R_{17}=R_{18}=R_{16}$, except when $R_{16}$ is H, and wherein $R_{16}$, $R_{17}$ and $R_{18}$ may be identical or different and, when $R_{16}$ is H, $R_{17}$ and $R_{18}$ may be identical or different.

5. The lubricant or the pressure transfer medium, as claimed in claim 1, wherein the one or more fatty acids and/or fatty acid derivatives contained therein is obtainable from one or more compounds selected from the group: oleic acid, linoleic acid, linolenic acid, palmitoleic acid, eicosenoic acid, erucic acid, methyl oleate, methyl linoleate, methyl linolenate, methyl palmitoleate, glycerol trioleate, glycerol trilinolate, glycerol trilinoleate, trimethylolpropane trioleate, trimethylolpropane trilinolate, trimethylolpropane trilinoleate, pentaerythritol tetraoleate, pentaerythritol tetralinolate, pentaerythritol tetralinoleate rapeseed oil, sunflower oil, palm oil, coconut oil, and olive oil.

6. A fatty acid and/or fatty acid derivative obtainable by acyloxylation of at least one double bond by radicals of neocarboxylic acids of the chemical formula V:

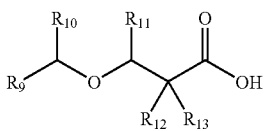

Formula V wherein $R_9$, $R_{10}$, $R_{12}$ and/or $R_{13}$ are identical or different and are hydrogen, straight-chain or branched alkyl, alkenyl or alkynyl radicals having up to 18 carbon atoms, cycloalkyl or cycloalkenyl radicals having from 5 to 8 carbon atoms, aryl, aralkyl or alkenylaryl radicals having from 6 to 16 carbon atoms or heterocyclic radicals, wherein each of the $R_9$ and $R_{10}$ and/or $R_{12}$ and $R_{13}$ radical pairs together with the carbon atom to which they are bonded may form a cycloalkane, cycloalkene or a heterocycle having from 5 to 7 ring members, and $R_9$, $R_{10}$, $R_{12}$ and $R_{13}$ may additionally carry substituents, and $R_{11}$ is hydrogen or a straight-chain or branched alkyl radical.

7. The fatty acid and/or fatty acid derivative as claimed in claim 6, wherein the neocarboxylic acids falling under the chemical formula V include those wherein $R_9$, $R_{10}$, $R_{12}$ and $R_{13}$ are identical or different and are hydrogen, straight-chain or branched alkyl radicals having from 1 to 12 carbon atoms, alkenyl or alkynyl radicals having from 2 to 12 carbon atoms, or wherein $R_9$, $R_{10}$, $R_{12}$ and $R_{13}$ are cycloalkyl or cycloalkenyl radicals having 5 or 6 carbon atoms, or are aryl, alkylaryl, aralkyl or alkenylaryl radicals having from 6 to 12 carbon atoms or heterocyclic radicals which contain one or more nitrogen and/or oxygen and/or sulfur atoms, and where $R_{11}$ is hydrogen or a straight-chain or branched alkyl radical having from 1 to 12 carbon atoms.

8. The lubricant or the pressure transfer medium, as claimed in claim 4, comprising one or more fatty acids and/or fatty acid derivatives selected from the group consisting of: 3-propyloxy-2,2-dimethylpropionic acid, 3-butyloxy-2,2-dimethylpropionic acid, 3-isobutyloxy-2,2-dimethylpropionic acid, 3-(2-ethylbutyloxy)-2,2-dimethylpropionic acid, 3-benzyloxy-2,2-dimethylpropionic acid and 3-(2-methylphenyloxy)-2,2-dimethylpropionic acid.

9. The lubricant or the pressure transfer medium of claim 4, wherein
   $R_{14}$ is selected from the group consisting of n-carboxyheptyl, n-carboxyundecyl, n-carboxy-4-heptenyl or esters thereof with monoalcohols, diols or polyols.

10. The lubricant or the pressure transfer medium of claim 4, wherein
    $R_{15}$ is selected from the group consisting of n-hexyl, n-octyl, 2-octenyl and 2,5-octadienyl.

11. The lubricant or the pressure transfer medium of claim 4 wherein
    $R_{16}$ is selected from the group consisting of
    methyl, ethyl, propyl, isopropyl, butyl, isobutyl, tertbutyl, pentyl, hexyl, octyl, decyl or cyclohexyl;
    phenyl, methyphenyl, ethylphenyl, misityl, cumyl, p-nitrophenylxylyl, hydroxyphenyl or naphthyl,
    benzyl, 1-phenylethyl, 2-phenylethyl, 2-phenyipropyl, cumylmethyl or misitylmethyl;
    methoxy, ethoxy, propyloxy, butyloxy, 2-ethylbutyloxy, 3-thiabutyloxy, 3-phosphabutyloxy;
    benzyloxy, 1-phenylethyloxy, (2-methyl)phenylmethoxy, p-sulfobenzyloxy and p-nitrobenzyloxy.

12. The lubricant or pressure transfer medium comprising one or more fatty acids and/or fatty acid derivatives of claim 6.

13. The lubricant or pressure transfer medium comprising one or more fatty acids and/or fatty acid derivatives of claim 7.

* * * * *